(12) United States Patent
Griveau et al.

(10) Patent No.: US 10,798,946 B2
(45) Date of Patent: Oct. 13, 2020

(54) METHOD FOR MANAGING FLEA BEETLES OF THE FAMILY CHRYSOMELIDAE IN BRASSICA CROPS

(71) Applicant: BASF Agrochemical Products B.V., Arnhem (NL)

(72) Inventors: Yannick Griveau, Mauer (DE); Eneko Barthaburu, Lyons (FR)

(73) Assignee: BASF AGROCHEMICAL PRODUCTS B.V., Arnhem (NL)

( * ) Notice: Subject to any disclaimer, the term of this patent is extended or adjusted under 35 U.S.C. 154(b) by 111 days.

(21) Appl. No.: 15/737,512

(22) PCT Filed: Jun. 8, 2016

(86) PCT No.: PCT/EP2016/062953
§ 371 (c)(1),
(2) Date: Dec. 18, 2017

(87) PCT Pub. No.: WO2016/202656
PCT Pub. Date: Dec. 22, 2016

(65) Prior Publication Data
US 2018/0153173 A1  Jun. 7, 2018

(30) Foreign Application Priority Data
Jun. 16, 2015  (EP) ................................. 15172302

(51) Int. Cl.
*A01N 63/00* (2020.01)
*A01N 63/10* (2020.01)
*A01N 63/30* (2020.01)
*A01N 25/00* (2006.01)
*A01N 25/26* (2006.01)
*A01N 43/40* (2006.01)
*A01N 43/50* (2006.01)
*A01H 5/10* (2018.01)
*C12N 15/82* (2006.01)

(52) U.S. Cl.
CPC .............. *A01N 63/10* (2020.01); *A01H 5/10* (2013.01); *A01N 25/00* (2013.01); *A01N 43/40* (2013.01); *A01N 43/50* (2013.01); *A01N 63/00* (2013.01); *A01N 63/30* (2020.01); *C12N 15/8274* (2013.01); *A01N 25/26* (2013.01); *C12Y 202/01006* (2013.01)

(58) Field of Classification Search
None
See application file for complete search history.

(56) References Cited

U.S. PATENT DOCUMENTS

| 6,551,962 B1 | 4/2003 | Perching et al. | |
|---|---|---|---|
| 2012/0149571 A1 | 6/2012 | Kloepper et al. | |
| 2016/0031948 A1* | 2/2016 | Thompson | C07K 14/32 504/101 |
| 2019/0216091 A1* | 7/2019 | Taghavi | A01N 53/00 |

FOREIGN PATENT DOCUMENTS

| CA | 2845408 A1 | * | 5/2014 | |
|---|---|---|---|---|
| CN | 1799315 A | * | 7/2006 | |
| CN | 103004885 A | * | 4/2013 | |
| CN | 104663725 A | * | 6/2015 | |
| JP | 2001346407 A | * | 12/2001 | |
| JP | 2009247302 A | * | 10/2009 | |
| WO | WO 2009/031031 | | 3/2009 | |
| WO | WO 2012/150335 | | 11/2012 | |
| WO | WO-2014082167 A1 | * | 6/2014 | ............... C12R 1/07 |
| WO | WO 2014/159630 | | 10/2014 | |

OTHER PUBLICATIONS

Mohamed et al.,Effect of plant growth promoting Bacillus subtilis and Pseudomonas fluor escens on growth and pigment composition of radish plants (*Raphanus sativus*) under NaCl stress, Photosynthetica (2012) , 50(2) , 263-272 (Year: 2012).*
Sapunova et al.,Effects of phytase producing bacteria *Bacillus* sp. F-12 and *Bacillus* sp. F—99 on germination of plant seeds and biochemical properties of soil Vestsi Natsyyanal ' nai Akademii Navuk Belarusi , Seryya Biyalagichnykh Navuk (2014) , (1) , 89-95 (Year: 2014).*
Badul et al., Treatment o f cabbage seeds against seed-borne diseases using bacteria, Proceedings—Microscopy Society of Southern (1998), 28, 46 (Year: 1998).*
Hu et al., Seed treatment containing Bacillus subtilis BY-2 in combination with other Bacillus isolates for control of Sclerotinia sclerotiorum on oilseed rape, Biological control (2019), vol. 133, pp . 50-57 (Year: 2019).*
Widnyana et al., Effect of seed soaking with *Bacillus* sp . and organic fertilizer on growth of mustard green, Asian Journal of Agriculture and Biology (2018) , vol. 6 , No. 2 , pp. 204-209, 15 refs , (Year: 2018).*
Ashlesha et al., Role of Panchgavya derived microbes in the management of damping-off of cauliflower seedlings , root rot of pea and collar rot of tomato, Plant Disease Research (Ludhiana) (2009) , vol. 24, No. 2, pp. 124-130, 25 refs , (Year: 2009).*
"Bulletin 545—2013 Corn", Control of Insect Pests of Field Crops, Jan. 1, 2013, pp. 1-3, Search Report.
Javaid, I., et al., "Trap Cropping in Insect Pest Management", Journal of Sustainable Agriculture, vol. 5, Issue 1-2, Jan. 1, 1995, pp. 117-136, Search Report.
Koul, Opender , "Microbial biopesticides: opportunities and challenges", CAB Reviews: Perspectives in Agriculture, Veterinary Science, Nutrition and Natural Resources, Jan. 1, 2011, vol. 6, No. 056, Search Report.

(Continued)

*Primary Examiner* — Alton N Pryor
(74) *Attorney, Agent, or Firm* — Marshall, Gerstein & Borun LLP

(57) ABSTRACT

The present invention relates to a method for managing flea beetles from the family of Chrysomelidae in *Brassica* crops. The invention further relates to seed and a kit of parts for use in this method. The invention also relates to the use of *Bacillus amyloliquefaciens* ssp. *plantarum* MBI600 for managing flea beetles in *Brassica* crops.

18 Claims, No Drawings

(56) References Cited

OTHER PUBLICATIONS

Metspalu, Luule, et al., "Flea beetle (Chrysomelidae: Alticinae) species composition and abundance in different cruciferous oilseed crops and the potential for a trap crop system", Acta Agriculturae Scandinavica, Section B—Soil & Plant Science, 2014, 64:7, 572-582, DOI: 10.1080/09064710.2014.933871.
Rossall, S., et al., "Some effects of Bacillus subtilis (MBI 600) on the development of cotton and peanut", Second International Workshop on Plant Growth-promoting Rhizobacteria, Jan. 1, 1991, pp. 88-92, Search Report.
Schmitt, A., et al., "STOVE: Seed treatments for organic vegetable production", The European Joint Organic Congress, Denmark, May 1, 2006, pp. 1-3, Search Report.
International Search Report dated Jul. 13, 2016, prepared in International Application No. PCT/EP2016/062953.
European Search Report dated Aug. 5, 2015, prepared in International Application No. 15172302.
International Preliminary Report on Patentability dated Dec. 19, 2017, prepared in International Application No. PCT/EP2016/062953.

* cited by examiner

METHOD FOR MANAGING FLEA BEETLES OF THE FAMILY CHRYSOMELIDAE IN BRASSICA CROPS

This application is a National Stage application of International Application No. PCT/EP2016/062953, filed Jun. 8, 2016. This application also claims priority under 35 U.S.C. § 119 to European Patent Application No. 15172302.0, filed Jun. 16, 2015.

The present invention relates to a method for managing flea beetles of the family Chrysomelidae in *Brassica* crops. The invention further relates to seed and a kit of parts for use in this method. The invention also relates to the use of *Bacillus amyloliquefaciens* ssp. *plantarum* MBI600 for managing flea beetles of the family Chrysomelidae in *Brassica* crops.

*Brassica* is a genus of Brassicaceae (Cruciferae) plant family. The genus is known for its important agricultural and horticultural crops that are extensively grown in numerous countries of the world. In most countries, the focus is on *Brassica napus*, *Brassica rapa* and *Brassica juncea* being valuable sources for the production of animal feed, edible oil and biodiesel. In order to reduce crop losses and to obtain optimal crop yield proper pest management is required.

Flea beetles of the family Chrysomelidae are the most chronic and economically damaging insect pests of *Brassica* crops. They are a challenge to manage because their emergence is difficult to forecast. Chrysomelidae can cause serious crop losses very quickly. In large numbers, they can rapidly defoliate and kill plants. The agriculturally most relevant species of Chrysomelidae damaging *Brassica* crops are *Phyllotreta cruciferae* (crucifer flea beetle) and *Phyllotreta striolata* (striped flea beetle).

Flea beetles are generally feeding on foliage of *Brassica* crops producing a shot-hole appearance and necrosis. Damage to the cotyledons and first true leaves delays plant development, causing unevenness in height and maturity as well as reduction of crop seed yields. The effect of the feeding activity varies with the plant development stage and the intensity of the attack. Although adult flea beetles can continue to cause some harm into the growing season, once plants are beyond the seedling stage, they are much less vulnerable to feeding damage and, at the two-leaf stage, plants are generally established enough to outgrow flea beetle injury.

The impact of the flea beetle feeding can be reduced by cultural (agronomic) practices that include reduced tillage, delayed planting etc. These practices, however, do not offer satisfactory results.

Insecticides are the most commonly used and currently preferred tool for managing flea beetles. In order to protect seedlings as soon as the plants emerge seeds can be treated with broad spectrum insecticides prior to planting. Acceleron™ and HELIX® (both thiamethoxam), GAUCHO®600 (imidacloprid), PONCHO®600 (clothianidin) and LUMIDERM™ (cyantraniliprole) insecticide seed treatments are registered for use on *Brassica napus*. Other seed treatments are known from e.g. WO 2014/159630. These insecticides are usually systemic and flea beetles must feed on the plant material to receive a lethal dose. Additionally, post-emergent insecticide application may be required to protect seedlings, which are exposed to severe or prolonged periods of intense attack. Reinvasion of the crop is also possible and a repeated treatment might be needed.

Another tool to manage flea beetles in *Brassica* crops is trap planting (*Acta Agriculurae Scandinavica*, Section B—Soil & Plant Science, 2014, Vol. 64, No. 7, 572-582).

The basic principle of trap planting is that insects have preference for trap plants and will move to them and not to the crop if given a choice. Therefore, trap plants can be planted along with the crop in order to entice insects away from the crop during a critical time period. The preference, however, is not absolute and flea beetles can additionally feed on the crop. Furthermore, trap plants compete with the crop for environmental resources and require procedures to eliminate the trap plants, latest at harvest.

Hence, there remains a need for methods of managing flea beetles in *Brassica* crops that provide for improved performance and overcome drawbacks of the known methods.

In particular, there is a need for methods preventing flea beetles of feeding on *Brassica* crops with sufficiently long action period.

There is also a need for methods that are environmentally friendly reducing or avoiding unfavorable environmental or toxicological effects whilst still providing effective flea beetle management in *Brassica* crops.

There is additionally a need for methods of managing flea beetles wherein the crop's exposure to insecticides is reduced.

It was therefore an object of the present invention to provide for a method of managing flea beetles in *Brassica* crops that meets one or more of the above needs.

We have found that this object and further objects are achieved by a method comprising
  a) planting seeds of a *Brassica* crop, which are covered by or mixed with a composition comprising a flea beetle repellant; and
  b) planting seeds of a trap plant, which are not covered by or mixed with a composition comprising a flea beetle repellant.

In a particular embodiment, the method comprises the following steps:
  i) planting
    a) seeds of an acetolactate synthase (ALS) inhibitor herbicide tolerant *Brassica* crop, which are covered by or mixed with a composition comprising a flea beetle repellant and
    b) seeds of an acetolactate synthase (ALS) inhibitor herbicide susceptible trap plant, which are not covered by or mixed with a composition comprising a flea beetle repellant;
  ii) applying a herbicidally active amount of an ALS-inhibitor herbicide to the *Brassica* crop and trap plants that grow from said seed or to their environment after the *Brassica* crop is mature enough to resist or overcome flea beetle damage.

Accordingly, said method is a subject matter of the present invention.

Surprisingly it has been found that the method according to the present invention provides for an improved flea beetle management in *Brassica* crops. In particular, flea beetles are kept from feeding on *Brassica* crops for sufficiently long period to let *Brassica* crop overgrow the seedling stage. Furthermore, the method is environmentally friendly due to the use of biological flea beetle repellents. Additionally, the crop's exposure to chemical insecticides is reduced or avoided.

Another subject matter of the present invention is seed comprising
  a) seeds of a *Brassica* crop, which are covered by or mixed with a composition comprising a flea beetle repellant; and
  b) seeds of a trap plant, which are not covered by or mixed with a composition comprising a flea beetle repellant.

The seed can be packed e.g. in form of a mixed seed pack or as a co-pack.

Another subject matter of the present invention is seed comprising
- a) seeds of an ALS-inhibitor herbicide tolerant *Brassica* crop, which are covered by or mixed with a composition comprising a flea beetle repellant; and
- b) seeds of an ALS-inhibitor herbicide susceptible trap plant, which are not covered by or mixed with a composition comprising a flea beetle repellant.

The seed can be packed e.g. in form of a mixed seed pack or as a co-pack.

Another subject matter of the present invention is a kit of parts comprising
- a) seeds of an ALS-inhibitor herbicide tolerant *Brassica* crop, which are covered by or mixed with a composition comprising a flea beetle repellant;
- b) seeds of an ALS-inhibitor herbicide susceptible trap plant, which are not covered by or mixed with a composition comprising a flea beetle repellant and.
- c) a composition comprising an ALS-inhibitor herbicide.

Another subject matter of the present invention is the use of *Bacillus amyloliquefaciens* ssp. *plantarum* MBI600, accession number NRRL B-50595, (R.4) to manage Chrysomelidae in *Brassica* crops.

Another subject matter of the present invention is the use of *Bacillus amyloliquefaciens* ssp. *plantarum* MBI600, accession number NRRL B-50595, (R.4) to manage flea beetles from the family of Chrysomelidae in *Brassica* crops.

Another subject matter of the present invention is the use of *Bacillus amyloliquefaciens* ssp. *plantarum* MBI600, accession number NRRL B-50595, (R.4) to manage Chrysomelidae in ALS-inhibitor herbicide tolerant *Brassica* crops.

Another subject matter of the present invention is the use of *Bacillus amyloliquefaciens* ssp. *plantarum* MBI600, accession number NRRL B-50595, (R.4) to manage flea beetles from the family of Chrysomelidae in ALS-inhibitor herbicide tolerant *Brassica* crops.

Further embodiments of the invention are evident from the claims, the description and the examples. It is to be understood that the single features of the subject matter of the invention described herein can be applied not only in the combination given in each particular case but also in other combinations, without leaving the scope of the invention.

As used herein, pesticidally, e.g. herbicidally, fungicidally, insecticidally etc., "active amount" means the amount of the inventive mixtures or of compositions comprising the mixtures needed to achieve an observable effect on growth, including the effects of necrosis, death, retardation, prevention, and removal, destruction, or otherwise diminishing the occurrence and activity of the target organism. The pesticidally active amount can vary for the various mixtures/compositions used in the invention. A pesticidally active amount of the mixtures/compositions will also vary according to the prevailing conditions such as desired pesticidal effect and duration, weather, target species, locus, mode of application, and the like.

As used herein, the term "agriculturally acceptable salts" refers to, but is not limited to, any chemical compound formed from the reaction of an acid with a base with all or part of the hydrogen of the acid replaced by a metal or any other cation. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)ammonium (diolamine salt), tris(2-hydroxyethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

As used herein, the term "agriculturally acceptable derivatives" refers to, but is not limited to, amides, esters and/or thioesters of compounds having a carboxyl group and/or an amino group. Examples of suitable amides are mono- and di-$C_1$-$C_6$-alkylamides or arylamides and the like.

Examples of suitable esters are allyl esters, propargyl esters, $C_1$-$C_{10}$-alkyl esters, alkoxyalkyl esters, tefuryl ((tetrahydrofuran-2-yl)methyl) esters and the like. Examples of suitable thioesters are $C_1$-$C_{10}$-alkylthio esters and the like. Preferred mono- and di-$C_1$-$C_6$-alkylamides are the methyl and the dimethylamides. Preferred arylamides are, for example, the anilides and the 2-chloroanilides. Preferred alkyl esters are, for example, the methyl, ethyl, propyl, isopropyl, butyl, isobutyl, pentyl, mexyl (1-methylhexyl), meptyl (1-methylheptyl), heptyl, octyl or isooctyl (2-ethylhexyl) esters. Preferred $C_1$-$C_4$-alkoxy-$C_1$-$C_4$-alkyl esters are the straight-chain or branched $C_1$-$C_4$-alkoxy ethyl esters, for example the 2-methoxyethyl, 2-ethoxyethyl, 2-butoxyethyl (butotyl), 2-butoxypropyl or 3-butoxypropyl ester. An example of a straight-chain or branched $C_1$-$C_{10}$-alkylthio ester is the ethylthio ester.

As used herein, the term "repellant" refers to a chemical, biochemical or biological agent (such as a virus, bacterium, etc.) repelling or tending to repel insects.

As used herein, the term "biopesticides" refers to pesticides based on micro-organisms (bacteria, fungi, viruses, nematodes, etc.) or natural products (compounds, such as metabolites, proteins, or extracts from biological or other natural sources) (U.S. Environmental Protection Agency: http://www.epa.gov/pesticides/biopesticides/). Biopesticides fall into two major classes, microbial and biochemical pesticides.

As used herein, the term "microbial pesticides" refers to biopesticides consisting of bacteria, fungi or viruses (and often include the metabolites that bacteria and fungi produce). Entomopathogenic nematodes are also classified as microbial pesticides, even though they are multi-cellular.

As used herein, the term "biochemical pesticides" refers to are naturally occurring substances or structurally-similar and functionally identical to a naturally-occurring substance and extracts from biological sources that control pests or provide other crop protection uses as defined below, but have non-toxic mode of actions (such as growth or developmental regulation, attractants, repellants or defense activators (e.g. induced resistance) and are relatively non-toxic to mammals.

The method according to the present invention exhibits a very good effect against flea beetles from the family Chrysomelidae.

In the context of the present invention, relevant are Chrysomelidae selected from the genus of *Phyllotreta, Psylliodes, Epitrix* and *Chaetocnemae*.

Examples of the relevant species from the genus of *Phyllotreta* are *Phyllotreta consobrina, Phyllotreta cruciferae, Phyllotreta diademata, Phyllotreta exclamation, Phyllotreta flexuosa, Phyllotreta nemorum, Phyllotreta nigripes, Phyllotreta nodicornis, Phyllotreta ochripes, Phyllotreta punctulata, Phyllotreta striolata, Phyllotreta tetrastigma, Phyllotreta undulata and Phyllotreta vittula*; most relevant are *Phyllotreta cruciferae, Phyllotreta nemorum, Phyllotreta striolata, Phyllotreta undulata and Phyllotreta vittula*.

Examples of the relevant species from the genus of *Psylliodes* are *Psylliodes affinis, Psylliodes attenuata, Psylliodes chalcomera, Psylliodes chrysocephala, Psylliodes cucullata, Psylliodes cuprea, Psylliodes dulcamarae, Psylliodes hyoscyami, Psylliodes laticollis, Psylliodes luridipennis, Psylliodes luteola, Psyllliodes marcida, Psylliodes napi, Psylliodes picina, Psylliodes punctulata and Psylliodes sophiae*; most relevant are *Psylliodes chrysocephala* and *Psylliodes punctulata*.

Example of the relevant species from the genus of *Epitrix* are *Epitrix atropae, Epitrix pubescens* and *Epitrix hirtipennis*; most relevant is *Epitrix hirtipennis*.

Examples of the relevant species from the genus of *Chaetocnemae* are *Chaetocnema aerosa, Chaetocnema arida, Chaetocnema concinna, Chaetocnema confuse, Chaetocnema hortensis, Chaetocnema picipes, Chaetocnema sahlbergii* and *Chaetocnema subcoerulea*; most relevant is *Chaetocnema confinis*.

In the context of the present invention, particularly relevant are Chrysomelidae flea beetles selected from *Phyllotreta cruciferae, Phyllotreta nemorum, Phyllotreta striolata, Phyllotreta undulata, Phyllotreta vittula, Psylliodes punctulata, Psylliodes chrysocephala, Epitrix hirtipennis* and *Chaetocnema confinis*, most relevant is *Psylliodes chrysocephala*.

According to the method of the present invention, the Chrysomelidae flea beetles are controlled in a *Brassica* crop.

According to a particular embodiment of the present invention, the Chrysomelidae flea beetles are controlled in a *Brassica* crop that is tolerant to an acetolactate synthase (ALS) inhibitor herbicide A.

Acetolactate synthase (ALS), also known as acetohydroxyacid synthase (AHAS), is an enzyme found in plants and microorganisms. ALS catalyzes the first step in the synthesis of branched chain amino acids such as valine, leucine, isoleucine. The enzyme typically comprises an acetohydroxyacid synthase large subunit (AHASL) and a small subunit. Further, at least three isozymes, namely AHAS1, AHAS2 and AHAS3, are known.

Acetolactate synthase (ALS) inhibitor herbicides (ALS-inhibitors) are herbicidally active compounds which inhibit the branched chain amino acid biosynthesis. They belong to group B of the HRAC classification system.

In a preferred embodiment, the ALS-inhibitor comprises one or more of the imidazolinone, sulfonylurea, triazolopyrimidine, pyrimidinyl benzoate and sulfonylamino carbonyl triazolinone herbicides or any mixture of the foregoing including agriculturally acceptable salts or derivatives thereof. Imidazolinone and sulfonylurea herbicides are preferred. Imidazolinone herbicides are most preferred Non-limiting preferred examples of ALS-inhibitors include
imidazolinones such as imazamethabenz, imazamethabenz-methyl, imazamox, imazapic, imazapyr, imazaquin and imazethapyr;
sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron;
triazolopyrimidine herbicides and sulfonanilides such as cloransulam, cloransulam-methyl, diclosulam, flumetsulam, florasulam, metosulam, penoxsulam, pyrimisulfan and pyroxsulam and triafamone;
pyrimidinyl benzoates (thiobenzoates and oxybenzoates) such as bispyribac, bispyribac-sodium, pyribenzoxim, pyriftalid, pyriminobac, pyriminobac-methyl, pyrithiobac, pyrithiobacsodium, 4-[[[2-[(4,6-dimethoxy-2-10 pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-di-methoxy-2-pyrimidinyl)oxy]benzenemethanamine (CAS 420138-01-8);
sulfonylaminocarbonyl-triazolinone herbicides such as flucarbazone, flucarbazone-sodium, propoxycarbazone, propoxycarbazone-sodium, thiencarbazone and thiencarbazone-methyl; or any mixture of the foregoing.

In a preferred embodiment, the ALS-inhibitor is selected from the group consisting of imazethapyr, imazaquin, imazamethabenz, imazamox, imazapic, imazapyr and any mixture of the foregoing including agriculturally acceptable salts or derivatives thereof.

In a more preferred embodiment, the ALS-inhibitor is selected from the group consisting of imazamox, imazethapyr, imazaquin, imazamethabenz, imazapic, imazapyr and any mixture of the foregoing including agriculturally acceptable salts or derivatives thereof.

In a most preferred embodiment, the ALS-inhibitor is selected from the group consisting of imazamox, imazethapyr, imazapyr and any mixture of the foregoing including agriculturally acceptable salts or derivatives thereof.

In an even more preferred embodiment, the ALS-inhibitor is imazamox or an agriculturally acceptable salt or derivative thereof.

In an equally preferred embodiment, the ALS-inhibitor is imazapic or an agriculturally acceptable salt or derivative thereof.

In another equally preferred embodiment, the ALS-inhibitor is imazethapyr or an agriculturally acceptable salt or derivative thereof.

In another equally preferred embodiment, the ALS-inhibitor is imazaquin or an agriculturally acceptable salt or derivative thereof.

In another equally preferred embodiment, the ALS-inhibitor is imazamethabenz or an agriculturally acceptable salt or derivative thereof.

In another equally preferred embodiment, the ALS-inhibitor is imazapyr or an agriculturally acceptable salt or derivative thereof.

In another preferred embodiment, the ALS-inhibitor is selected from the group consisting of sulfonylureas selected from amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron.

In a more preferred embodiment, the ALS-inhibitor is selected from the group consisting of amidosulfuron, azimsulfuron, bensulfuron-methyl, chlorimuron-ethyl, chlorsulfuron, cyclosulfamuron, ethametsulfuron-methyl, ethoxysulfuron, flazasulfuron, flucetosulfuron, flupyrsulfuron-methyl-sodium, foramsulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron-methyl, nicosulfuron, orthosulfamuron, oxasulfuron, primisulfuron-methyl, propyrisulfuron, prosulfuron, pyrazosulfuron-ethyl, rimsulfuron, sulfometuron-methyl, sulfosulfuron, thifensulfuron-methyl, triasulfuron, tribenuron-methyl, trifloxysulfuron, triflusulfuron-methyl, tritosulfuron and any mixture of the foregoing including agriculturally acceptable salts or derivatives thereof.

In a most preferred embodiment, the ALS-inhibitor is selected from the group consisting of bensulfuron-methyl, cyclosulfamuron, flupyrsulfuron-methyl-sodium, foramsulfuron, imazosulfuron, iodosulfuron, iodosulfuron-methyl-sodium, iofensulfuron, iofensulfuron-sodium, mesosulfuron, metazosulfuron, nicosulfuron, propyrisulfuron, pyrazosulfuron-ethyl, rimsulfuron, sulfosulfuron, thiencarbazon-methyl, tribenuron-methyl, tritosulfuron and any mixture of the foregoing including agriculturally acceptable salts or derivatives thereof;

In yet another equally preferred embodiment, the ALS-inhibitor is tribenuron or an agriculturally acceptable salt or derivative thereof.

The above mentioned ALS-inhibitors including agriculturally acceptable salts and derivatives thereof are known herbicides, see, for example, The Pesticide Manual, 13th Edition, British Crop Protection Council (2003) or The Compendium of Pesticide Common Names (http://www.alan-wood.net/pesticides/).

The *Brassica* crop according to the present invention is preferably selected from *Brassica napus, Brassica juncea* and *Brassica rapa*.

In a preferred embodiment, the *Brassica* crop is *Brassica napus*.

In an equally preferred embodiment, the *Brassica* crop is *Brassica rapa*.

In yet equally preferred embodiment, the *Brassica* crop is *Brassica juncea*.

The ALS-inhibitor tolerant *Brassica* crop according to the present invention is preferably selected from *Brassica napus, Brassica juncea* and *Brassica rapa*.

In a preferred embodiment, the ALS-inhibitor tolerant *Brassica* crop is *Brassica napus*.

In an equally preferred embodiment, the ALS-inhibitor tolerant *Brassica* crop is *Brassica rapa*.

In yet equally preferred embodiment, the ALS-inhibitor tolerant *Brassica* crop is *Brassica juncea*.

In one embodiment, the ALS-inhibitor tolerant *Brassica* crop contains an ALS-inhibitor tolerance trait, wherein the AHASL protein comprises at least one amino acid substitution.

In one preferred embodiment, the ALS-inhibitor tolerant *Brassica* crop contains an AHASL trait that has a substitution(s) at least one of the positions A122(At), P197(At), R199(At), T203(At), A205(At), W574(At), S653(At), or G654(At). An A122(At)T substitution is preferred.

In another preferred embodiment, the ALS-inhibitor tolerant *Brassica* crop contains an AHASL trait having two substitutions, an A122(At) T substitution and an S653(At)N substitution. Preferably, the AHASL trait is the *Brassica napus* A-genome AHASL gene.

In another preferred embodiment, the ALS-inhibitor tolerant *Brassica* crop contains both an AHASL trait having two substitutions, an A122(At) T substitution and an S653(At)N substitution as well as one or two additional AHASL trait(s) that each have substitution(s) at least one of the positions A122(At), P197(At), R199(At), T203(At), A205(At), W574(At), S653(At), or G654(At).

In another preferred embodiment, the ALS-inhibitor tolerant *Brassica* crop contains both an AHASL trait having one S653(At)N substitution and an additional AHASL trait that has one substitution of A122(At)T, A122(At)Q, or W574(At)L.

In another preferred embodiment, the ALS-inhibitor tolerant *Brassica* crop has a trait having an S653(At)N substitution of the AHAS1 enzyme and/or a W574(At)L substitution of the AHAS3 enzyme. An example of said *Brassica* crop include, but is not limited to, the oil seed rape of Clearfield® OSR (BASF) which is, for example, tolerant towards imidazolinone herbicides.

In another preferred embodiment, the ALS-inhibitor tolerant *Brassica* crop as described in the previous embodiments further expresses an insecticidal protein. The insecticidal protein is preferably selected from the *Bacillus* Cry and Vip toxins.

The ALS-inhibitor tolerant *Brassica* crop includes naturally occurring plants as well as plants that have been modified by breeding, mutagenesis or genetic engineering, e.g. have been rendered tolerant to applications of ALS-inhibitor herbicides. Furthermore, plants that have been made tolerant to multiple classes of herbicides through multiple genetic modifications, such as tolerance to both ALS inhibitors and glyphosate are also within the scope of the present invention. These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Examples of these herbicide resistance technologies are also described in US 2008/0028482, US2009/0029891, WO 2007/143690, WO 2010/080829, U.S. Pat. Nos. 6,307,129, 7,022,896, US 2008/0015110, U.S. Pat. Nos. 7,632,985, 7,105,724, and 7,381,861, each herein incorporated by reference. Particular example of cultivated plants rendered tolerant to herbicides by conventional methods of breeding (mutagenesis) is Clearfield® summer rape (Canola, BASF SE, Germany) being tolerant to imidazolinones, e. g. imazamox. The Clearfield® summer rape is a particularly preferred *Brassica* crop according to the present invention.

Furthermore, the ALS-inhibitor tolerant *Brassica* crop includes genetically modified plants. The term "genetically modified plants" is to be understood as plants, which genetic material has been modified by the use of recombinant DNA techniques in a way that under natural circumstances it cannot readily be obtained by cross breeding, mutations, natural recombination, breeding, mutagenesis, or genetic engineering. Typically, one or more genes have been integrated into the genetic material of a genetically modified plant in order to improve certain properties of the plant. Such genetic modifications also include, but are not limited to, targeted post-translational modification of protein(s), oligo- or polypeptides e. g. by glycosylation or polymer additions such as prenylated, acetylated or farnesylated moieties or PEG moieties. The methods for generating genetically modified plants are generally known to the person skilled in the art.

Furthermore, *Brassica* crop includes plants that are by the use of recombinant DNA techniques capable to synthesize one or more insecticidal proteins, especially those known from the bacterial genus *Bacillus*, particularly from *Bacillus thuringiensis*, such as endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of arthropods, especially to beetles (*Coeloptera*), two-winged insects (*Diptera*), and moths (*Lepidoptera*) and to nematodes (*Nematoda*).

Moreover, *Brassica* crop includes plants that are derived from the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes or T4-lysozym. The methods for producing such genetically modified plants are generally known to the person skilled in the art and are described, e.g. in the publications mentioned above.

Furthermore, *Brassica* crop includes plants that are created by the use of recombinant DNA techniques which are capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, *Brassica* crop includes plants that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, *Brassica* crop includes plants that contain by the use of recombinant DNA techniques a modified amount of substances of content or new substances of content, specifically to improve raw material production, e.g. potatoes that produce increased amounts of amylopectin.

The trap plants according to the present invention are susceptible to ALS-inhibitors.

The particular trap plant may be more attractive, less attractive or of the same attractiveness to the flea beetles as the particular *Brassica* crop. Preference is given to more attractive trap plants or to trap plants of the same attractiveness. Particular preference is given to more attractive trap plants.

Preferably, the ALS-inhibitor susceptible trap plants are selected from the family Brassicaceae.

In particular, the ALS-inhibitor susceptible Brassicaceae trap plants are selected from the genus of *Brassica, Camelina, Eruca, Raphanus* and *Sinapis*. *Brassica* trap plants are preferred.

Examples of the ALS-inhibitor susceptible trap plants from the genus of *Brassica* are *Brassica alba, Brassica campestris, Brassica elongata, Brassica fruticulosa, Brassica hirta, Brassica incana* (=*Brassica geniculata*), *Brassica juncea, Brassica napus, Brassica nigra, Brassica rapa* and *Brassica tournefortii*, preferred are *Brassica campestris, Brassica juncea, Brassica napus, Brassica nigra* and *Brassica rapa*.

Examples of the ALS-inhibitor susceptible trap plants from the genus of *Camelina* are *Camelina microcarpa* and *Camelina sativa*, preferred is *Camelina sativa*.

Examples of the ALS-inhibitor susceptible trap plants from the genus of *Eruca* are *Eruca sativa* and *Eruca vesicaria*, preferred is *Eruca sativa*.

Examples of the ALS-inhibitor susceptible trap plants from the genus of *Raphanus* are *Raphanus raphanistrum* and *Raphanus sativus*, preferred is *Raphanus sativus*.

Examples of the ALS-inhibitor susceptible trap plants from the genus of *Sinapis* are *Sinapis alba, Sinapis arvensis* and *Sinapis incana*, preferred is *Sinapis alba*.

Particularly preferred ALS-inhibitor susceptible trap plants are selected from *Brassica campestris, Brassica juncea, Brassica napus, Brassica nigra, Brassica rapa, Camelina sativa, Eruca sativa, Raphanus sativus* and *Sinapis alba*.

The most preferred ALS-inhibitor susceptible trap plant is *Sinapis alba*.

In one embodiment of the present invention, the seeds of the trap plants are planted in an arrangement such that the resulting trap plants are surrounding (perimeter trap cropping), alternating (row or string trap cropping) or mixed with the ALS-inhibitor herbicide-tolerant *Brassica* crop. Perimeter or alternating trap cropping is more preferred. Perimeter trap cropping is most referred.

According to the present invention, the seeds of the *Brassica* crop are covered by or mixed with a composition comprising an insect repellant, in particular a flea beetle repellant.

The repellants are usually selected from biopesticides, synthetic repellant compounds, herbal repellant compounds and any mixtures thereof.

Preferably, the repellants are selected from biopesticides, more preferably from microbial pesticides, discouraging Chrysomelidae flea beetles from landing and/or feeding on *Brassica* crops, preferably on the leaves thereof. They may additionally have acaricidal, bactericidal, fungicidal, insecticidal, molluscidal, nematicidal, pheromone, viricidal, plant defense activator, plant stress reducing, plant growth regulator, plant growth promoting and/or yield enhancing activity.

Particularly preferred repellants are selected from the genus of *Bacillus, Burkholderia, Coniothyrium, Paecilomyces, Paenibacillus, Penicillium* and *Pasteuria*.

Many of these biopesticides have been deposited under deposition numbers mentioned herein (the prefixes refer to the acronym of the respective culture collection), are referred to in literature, registered and/or are commercially available.

Preferably, the repellant is selected from the genus of *Bacillus*, e.g. from:

R.1. *Bacillus amyloliquefaciens* spp. *plantarum* D747 (US 20130236522 A1; FERM BP-8234; e. g. Double Nickel™ 55 WDG or Double Nickel™ LC from Certis LLC, USA), R.2 *Bacillus amyloliquefaciens* spp. *plantarum* FZB24 isolated from plant pathogen-infested soil of a sugar beet field in Brandenburg, Germany (also called SB3615; DSM ID 96-2; J. Plant Dis. Prot. 105, 181-197, 1998; e. g. Taegro® from Novozyme Biologicals, Inc., USA), R.3 *Bacillus amyloliquefaciens* ssp. *plantarum* FZB42 isolated from plant pathogen-infested soil of a sugar beet field in Brandenburg, Germany (J. Plant Dis. Prot. 105, 181-197, 1998; DSM 23117; e. g. RhizoVital® 42 from AbiTEP GmbH, Berlin, Germany), R.4 *Bacillus amyloliquefaciens* ssp. *plantarum* MBI600 also referred to as 1430 (NRRL B-50595; Int. J. Microbiol. Res. 3(2) (2011), 120-130; US 2012/0149571 A1; e. g. Integral®, Subtilex® NG from BASF Corp., USA), R.5 *Bacillus amyloliquefaciens* ssp. *plantarum* QST-713, (=*Bacillus subtilis* QST-713) isolated from a California peach orchard in 1995 (NRRL B-21661; e. g. Rhapsody®, Serenade® MAX or Serenade® ASO from AgraQuest Inc., USA), R.6 *Bacillus amyloliquefaciens* spp. *plantarum* TJ1000 (also called 1BE; CA 2471555 A1; ATCC BAA-390; e. g. QuickRoots™ from TJ Technologies, Watertown, S. Dak., USA), R.7 *Bacillus firmus* I-1582 (WO 2009/126473, WO 2009/124707, U.S. Pat. No. 6,406,690; CNCM 1-1582 e. g. Votivo® from Bayer CropScience LP, USA), R.8 *Bacillus pumilus* GHA 180 isolated from apple tree rhizosphere in Mexico (IDAC 260707-01; e. g. in PROMIX® BX from Premier Horticulture, 1, avenue Premier, Rivie're-du-Loup, Quebec, Canada G5R6C1), R.9 *Bacillus pumilus* INR-7 otherwise referred to as BU F22 and BU-F33 (NRRL B-50185, NRRL B-50153; U.S. Pat. No. 8,445,255), R.10 *Bacillus pumilus* QST 2808 (NRRL B-30087; e. g. Sonata® or Ballad® Plus from AgraQuest Inc., USA), R.11 *Bacillus simplex* ABU 288 (NRRL B-50340, US 2012/0149571) and R.12 *Bacillus subtilis* FB17 also called UD 1022 or UD10-22 isolated from red beet roots in North America (ATCC PTA-11857; System. Appl. Microbiol. 27, 372-379, 2004; US 2010/0260735; WO 2011/109395);

Preference is given to R.4.

Equally preferred are repellants selected from the genus of *Burkholderia*, e.g.

R.13 *Burkholderia* sp. A396 (NRRL B-50319; WO 2013/032693; Marrone Bio Innovations, Inc., USA).

Equally preferred are repellants selected from the genus of *Coniothyrium*, e.g

R.14 *Coniothyrium minitans* CON/M/91-08 (WO 1996/021358; DSM 9660; e. g. Contans® WG, Intercept® WG from Prophyta Biologischer Pflanzenschutz GmbH, Germany).

Equally preferred are repellants selected from the genus of *Paecilomyces*, e.g.

R.15 *Paecilomyces lilacinus* 251 isolated from infected nematode eggs in the Philippines (AGAL 89/030550; WO1991/02051; Crop Protection 27, 352-361, 2008; e. g. Bio-Act®/MeloCon® from Prophyta, Germany).

Equally preferred are repellants selected from the genus of *Paembacillus*, e.g.

R.16 *Paembacillus alvei* NAS6G6 (WO 2014/029697; NRRL B-50755; e.g. BAC-UP from BASF Agricultural Specialities (Pty) Ltd., South Africa in mixture with *Bacillus pumilus* KFP9F).

Equally preferred are repellants selected from the genus of *Penicillium*, e.g.

R.17 *Penicillium bilaiae* (also called *P. bilaii*) strains ATCC 18309 (=ATCC 74319), ATCC 20851 and/or ATCC 22348 (=ATCC 74318) originally isolated from soil in southern Alberta (Fertilizer Res. 39, 97-103, 1994; Can. J. Plant Sci. 78(1), 91-102, 1998; U.S. Pat. No. 5,026,417, WO 1995/017806; e. g. Jump Start®, Provide® from Novozymes Biologicals BioAg Group, Canada).

Equally preferred are repellants selected from the genus of *Pasteuria*, e.g.

R.18 *Pasteuria nishizawae* Pn1 (ATCC SD-5833, isolated from an Illinois soybean field, Pesticide Chemical (PC) Code: 016455; WO 2010/80169).

More preferred are repellants selected from the genus of *Bacillus*, in particular R.4.

Strains can be obtained from culture collections and deposition centers (listed by their acronym=strain prefix here: http://www.wfcc.info/ccinfo/collection/by_acronym/) such as strains with prefixes:

AGAL: National Measurement Institute, 1/153 Bertie Street, Port Melbourne, Victoria, Australia 3207;

ATCC: American Type Culture Collection, 10801 University Blvd., Manassas, Va. 20110-2209, USA;

CNCM: Collection Nationale de Cultures de Microorganismes, Institute Pasteur, 25 rue du Docteur Roux, F-75724 PARIS Cedex 15;

DSM: Leibniz-Institut DSMZ-Deutsche Sammlung von Mikroorganismen and Zellkulturen GmbH, Inhoffenstraße 7 B, 38124 Braunschweig, Germany;

IDAC: International Depositary Authority of Canada Collection, Canada;

NRRL: ARS Culture Collection of the National Center for Agricultural Utilization Research, Agricultural Research Service, U.S. Department of Agriculture, 1815 North University Street, Peoria, Ill. 61604, USA;

Further strains may be found at: http://gcm.wfcc.info/; http://www.landcareresearch.co.nz/resources/collections/icmp.

Alternatively, the repellants R.1 to R.18 can be cultivated continuously or discontinuously in the batch process or in the fed batch or repeated fed batch process. A review of known methods of cultivation will be found in the textbook by Chmiel (Bioprozesstechnik 1. Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)). The culture medium that is to be used must satisfy the requirements of the particular strains in an appropriate manner. Descriptions of culture media for various microorganisms are given in the handbook "Manual of Methods for General Bacteriology" of the American Society for Bacteriology (Washington D.C., USA, 1981).

The repellants R.1 to R.18 embrace not only the isolated, pure cultures of the respective microorganism as defined herein, but also its cell-free extract, its suspensions in a whole broth culture or as a metabolite-containing supernatant or a purified metabolite obtained from a whole broth culture of the microorganism or microorganism strain.

The repellants R.1 to R.18 embraces not only the isolated, pure cultures of the respective micro-organism as defined herein, but also a cell-free extract thereof or a metabolite thereof, and/or a mutant of the respective micro-organism having all the identifying characteristics thereof and also a cell-free extract or at least one metabolite of the mutant.

The repellants R.1 to R.18 may be isolated or substantially purified. The terms "isolated" or "substantially purified" refers to microbial pesticides that have been removed from a natural environment and have been isolated or separated, and are at least 60% free, preferably at least 75% free, and more preferably at least 90% free, even more preferably at least 95% free, and most preferably at least 100% free from other components with which they were naturally associated. An "isolated culture" or "substantially purified culture" refers to a culture of the microbial pesticides that does not include significant amounts of other materials such as other materials which normally are found in natural habitat in which the microbial pesticides grows and/or from which the microbial pesticides normally may be obtained. An "isolated culture" may be a culture that does not include any other biological, microorganism, and/or bacterial species in quantities sufficient to interfere with the replication of the isolated culture. Isolated cultures of microbial pesticides may, however, be combined to prepare a mixed culture of microbial pesticides.

Herein, the repellants R.1 to R.18 may be supplied in any physiological state such as active or dormant. Dormant microbial pesticides may be supplied for example frozen, dried, or lyophilized or partly desiccated (procedures to produce partly desiccated organisms are given in WO 2008/002371) or in form of spores.

The repellants R.1 to R.18 used as organism in an active state can be delivered in a growth medium without any additional additives or materials or in combination with suitable nutrient mixtures.

Examples of suitable synthetic repellants are 2,3,4-tri-O-acylhexose derivatives (see e.g. U.S. Pat. No. 4,943,563) and the compounds described in U.S. Pat. No. 5,661,181.

Examples of suitable herbal repellants are *Artemisia* oil; *Azadirachta* oil (=Neem oil); *Mentha* oil (=mint oil); cilantro (*Coriandrum*) oil, citrus oil, *Allium* juce, e.g. garlic or onion juice; beta-io-none, d-limonene, *Capsicum*/capsaicin and diatomaceous earth.

In one embodiment of the present invention, the composition comprising a repellant comprises a biopesticide insect repellant, a synthetic repellant or a herbal repellant.

In another embodiment of the present invention, the composition comprising a repellant comprises a biopesticide insect repellant and a synthetic and/or a herbal repellant.

For the purposes of seed covering, the repellants can be converted into customary types of agrochemical compositions comprising said repellants, and, if desired, a suitable auxiliary.

Examples of agrochemical compositions suitable for seed covering are solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed. These and further compositions types are defined in the "Catalogue of pesticide formulation types and international coding system", Technical Monograph No. 2, 6th Ed. May 2008, CropLife International.

Herein, it has to be taken into account that each formulation type should not influence the viability of the microorganism during storage of the composition and when finally applied to seed. Suitable formulations are e.g. mentioned in WO 2008/002371, U.S. Pat. Nos. 6,955,912, 5,422,107.

According to one embodiment, the agrochemical compositions for seed coveting contain the repellants in an amount from $1\times10^5$ to $1\times10^{12}$ CFU, preferably from $1\times10^7$ CFU to $1\times10^{12}$ CFU, more preferably from $1\times10^9$ CFU to $1\times10^{12}$ CFU per gram total weight of the composition.

The application rates of the repellants with respect to the seeds preferably range from about $1\times10^6$ to $1\times10^{12}$ (or more) CFU/seed. Preferably, the concentration is about $1\times10^6$ to about $1\times10^9$ CFU/seed. The application rates of the repellants of the present invention with respect to the seeds also preferably range from about $1\times10^7$ to $1\times10^{14}$ (or more) CFU per 100 kg of seed, preferably from $1\times10^9$ to about $1\times10^{12}$ CFU per 100 kg of seed.

"CFU" (colony forming unit) is a measure of viable microbial cells, in particular fungal and bacterial cells, in a sample. The total weight of the respective repellant in an agrochemical composition can be calculated using the following equation: $1\times10^{10}$ CFU=1 gram of total weight of the repellant.

Typically, a pre-mix agrochemical composition for seed covering application comprises 0.5 to 99.9 percent, especially 1 to 95 percent, of the desired active ingredients, and 99.5 to 0.1 percent, especially 99 to 5 percent, of a solid or liquid adjuvant (including, for example, a solvent such as water), where the auxiliaries can be a surfactant in an amount of 0 to 50 percent, especially 0.5 to 40 percent, based on the pre-mix formulation. Whereas commercial products will preferably be formulated as concentrates (e.g., pre-mix composition (formulation)), the end user will normally employ dilute formulations (e.g., tank mix composition).

The agrochemical compositions comprising repellants can additionally comprise one or more agriculturally useful compounds, e.g. fungicides, plant growth regulators and fertilizers.

As used herein, the term "fungicide" comprises biocidal chemical compounds or biological organisms used to kill or inhibit fungi or fungal spores. Examples of fungicides include, but are not limited to, storbilurins, carboxamides, azoles, heterocyclic compounds, carbamates and other active compounds.

Examples for useful strobilurins include, but are not limited to, azoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, methyl (2-chloro-5[1-(3-methylbenzyloxyimino)ethyl]benzyl)carbamate and 2(2-(3-(2,6-dichlorophenyl)-1-methyl-al-lylideneaminooxymethyl)-phenyl)-2-methoxyimino-N methylacetamide.

Examples for useful carboxamides include, but are not limited to carboxanilides including benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, penflufen, penthiopyrad, sedaxane, tecloftalam, thifluzamide, tiadinil, 2-amino-4 methyl-thiazole-5-carboxanilide, N-(3',4',5' trifluorobiphenyl-2 yl)-3-difluoro-methyl-1-methyl-1H-pyrazole-4 carboxamide, N-(4'-trifluoromethylthiobiphenyl-2-yl)-3 difluoromethyl-1-methyl-1H pyrazole-4-carboxamide and N-(2-(1,3,3-trimethyl-butyl)-phenyl)-1,3-dimethyl-5 fluoro-1H-pyrazole-4 carboxamide; carboxylic morpholides including dimethomorph, flumorph, pyrimorph; benzoic acid amides including flumetover, fluopicolide, fluopyram, zoxamide; and other carboxamides including carpropamid, dicyclomet, mandipromid, oxytetracyclin, silthiofarm and N-(6-methoxy-pyridin-3-yl) cyclopropanecarboxylic acid amide.

Examples for useful azoles include, but are not limited to, triazoles including azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole; imidazoles including cyazofamid, imazalil, pefurazoate, prochloraz, triflumizol; benzimidazoles including benomyl, carbendazim, fuberidazole, thiabendazole; and others azoles including ethaboxam, etridiazole, hymexazole and 2-(4-chloro-phenyl)-N-[4-(3,4-di-methoxy-phenyl)-isoxazol-5-yl]-2-prop-2-ynyloxy-acetamide.

Examples for useful heterocyclic compounds include, but are not limited to, pyridines including fluazinam, pyrifenox, 3-[5-(4-chloro-phenyl)-2,3-dimethyl-isoxazolidin-3 yl]-pyridine, 3-[5-(4-methyl-phenyl)-2,3-dimethyl-isoxazolidin-3-yl]-pyridine; pyrimidines including bupirimate, cyprodinil, diflumetorim, fenarimol, ferimzone, mepanipyrim, nitrapyrin, nuarimol, pyrimethanil; Piperazines including triforine; pyrroles including fenpiclonil, fludioxonil; morpholines including aldimorph, dodemorph, dodemorph-acetate, fenpropimorph, tridemorph; piperidines including fenpropidin; dicarboximides including fluoroimid, iprodione, procymidone, vinclozolin; non-aromatic 5-membered heterocycles including famoxadone, fenamidone, flutianil, octhilinone, probenazole, 5-amino-2-isopropyl-3-oxo-4-ortho-tolyl-2,3-dihydro-pyrazole-1 carbothioic acid S-allyl ester; and other heterocyclic compounds including acibenzolar-S-methyl, ametoctradin, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quin-oxyfen, triazoxide, tricyclazole, 2-butoxy-6-iodo-3-propylchromen-4-one, 5-chloro-1 (4,6-dimethoxy-pyrimidin-2-yl)-2-methyl-1H-benzoimidazole and 5 chloro-7 (4-methylpiperidin-1-yl)-6-(2,4,6-trifluorophenyl)-[1,2,4]triazolo[1,5 a]pyrimidine.

Examples for useful carbamates include, but are not limited to, thio- and dithiocarbamates including ferbam, mancozeb, maneb, metam, methasulphocarb, metiram, propineb, thiram, zineb, ziram; other carbamates including benthiavalicarb, diethofencarb, iprovalicarb, propamocarb, propamocarb hydrochlorid, valifenalate and N-(1-(1-(4-cyano-phenyl)ethanesulfonyl)-but-2-yl) carbamic acid-(4-fluorophenyl) ester.

Examples for useful other active substances include, but are not limited to, guanidines including guanidine, dodine, dodine free base, guazatine, guazatine-acetate, iminoctadine, iminoctadine-triacetate, iminoctadine-tris(albesilate); antibiotics including kasugamycin, kasugamycin hydrochloride-hydrate, streptomycin, polyoxine, validamycin A; nitrophenyl derivates including binapacryl, dinobuton, dinocap, nitrthal-isopropyl, tecnazen; organometal compounds including fentin salts, such as fentin-acetate, fentin chloride or fentin hydroxide; sulfur-containing heterocyclyl compounds including dithianon, isoprothiolane; organophosphorus compounds including edifenphos, fosetyl, fosetyl-aluminum, iprobenfos, phosphorous acid and its salts, pyrazophos, tolclofos-methyl; organochlorine compounds including chlorothalonil, dichlofluanid, dichlorophen, flusulfamide, hexachlorobenzene, pencycuron, pentachlorphenole and its salts, phthalide, quintozene, thiophanate-methyl, tolylfluanid, N-(4-chloro-2-nitro-phenyl)-N-ethyl-4-methyl-benzenesulfonamide; inorganic active substances including Bordeaux mixture, copper acetate, copper hydroxide, copper oxychloride, basic copper sulfate, sulfur; and other active substances including biphenyl, bronopol, cyflufenamid, cymoxanil, diphenylamin, metrafenone, mildiomycin, oxincopper, prohexadione-calcium, spiroxamine, tebufloquin, tolylfluanid, N-(cyclo-propyl-methoxyimino-(6-difluoromethoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N methyl formamidine, N'(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2 methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydronaphthalen-1-yl-amide, methoxy-acetic acid 6-tert-butyl-8-fluoro-2,3-dimethyl-quinolin-4-yl ester and N-Methyl-2-{1-

[(5-methyl-3-trifluoromethyl-1H-pyrazol-1-yl)-acetyl]-piperidin-4-yl}-N-[(1R)-1,2,3,4-tetrahydro-naphthalen-1-yl]-4-thiazolecarboxamide.

Preferred fungicides are selected from dimethomorph (F.1), pyraclostrobin (F.2), boscalid (F.3), thiram (F.4), metalaxyl (F.5), metalaxyl-M (mefenoxam) (F.6), fludioxonil (F.7) and sedaxane (F.8).

In one embodiment of the present invention, the composition for covering seeds of *Brassica* crop comprise a flea beetle repellant R.4 and a fungicide F selected from F.1, F.2, F.3, F.4, F.5, F.6, F.7 or F.8.

As used herein, the term "plant growth regulators" (PGR) refers to compounds that may interact with the hormonal system of the treated plants and regulate the growth of a plant or parts of a plant. They may affect developmental processes and differentiation in plants at low dosages without having a nutritive value or being phytotoxic. More specifically, various PGRs can, for example, reduce plant height, stimulate seed germination, induce flowering, darken leaf coloring, minimize lodging of cereals, change the rate of plant growth and modify the timing and efficiency of flowering, fruit formation, ripening, fruit drop, defoliation or quality traits. There are several different classes of plant growth regulators. Known classes include, but are not limited to, azoles (such as uniconazole and paclobutrazol), cyclohexane carboxylates (such as trinexapac, trinexapac-ethyl, prohexadione and prohexadione-calcium), pyrimidinyl carbinols (such as flurprimidol and ancymidol), quarternary ammoniums (such as chlormequat-chloride and mepiquat-chloride) and sulphonyl-amino phenyl-acetamides (such as mefluidide). Examples of useful growth regulators include, but are not limited to, abscisic acid, amidochlor, ancymidol, 6-benzyl-aminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N 6 benzyladenine, paclobutrazol, prohexadione (prohexadione-calcium), prohydrojasmon, thidiazuron, triapenthenol, tributyl phosphorotrithioate, 2,3,5 tri iodobenzoic acid, trinexapac-ethyl and uniconazole.

As used herein the term "fertilizer" refers to any substance that is added to the soil to help the growth of plants. Examples of fertilizers include, but not limited to, ammonium sulfate, ammonium phosphate, ammonium nitrate, and ureas.

The agrochemical compositions comprising repellants according to the present invention can comprise at least one auxiliary (inert ingredient) and be prepared by usual means (see e.g. H. D. Burges: Formulation of Micobial Biopesticides, Springer, 1998).

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellants, attractants, feeding stimulants, compatibilizers, bactericides, anti-freezing agents, anti-foaming agents, colorants, tackifiers and binders. Care must be taken that the choice and amounts of such auxiliaries, in particular of those listed below, should not influence the viability of the microbial pesticides in the composition. Especially for bactericides and solvents, compatibility with the respective microorganism of the respective microbial pesticide has to be taken into account.

Suitable solvents and liquid carriers are water and organic solvents, such as mineral oil fractions of medium to high boiling point, e.g. kerosene, diesel oil; oils of vegetable or animal origin;

aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or akylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a negligible or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), inorganic clays (organically modified or unmodified), polycarboxylates, and silicates.

Suitable bactericides are bronopol and isothiazolinone derivatives such as alkyliso-thiazolinones and benzisothiazolinones. Suitable anti-freezing agents are ethylene glycol, propylene glycol, urea and glycerin. Suitable anti-foaming agents are silicones, long chain alcohols, and salts of fatty acids. Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants). Suitable tackifiers or binders are polyvinylpyrrolidones, polyvinylacetates, polyvinyl alcohols, polyacrylates, biological or synthetic waxes, and cellulose ethers.

According to the present invention, the seeds of the *Brassica* crop are covered by or mixed with a composition comprising an insecticide repellant.

The term "covered" as used herein refers to the placing compositions comprising repellants of the present invention onto the entire seed or on only parts thereof, including on only a single side or a portion of a single side. One of ordinary skill in the art would understand these application methods from the description provided in EP954213B1 and WO06/112700.

Seed covering can vary from a thin film (dressing) of the respective composition on a seed, where the original size and/or shape are recognizable to an intermediary state (such as a coating) and then to a thicker film (such as pelleting with many layers of different materials (such as carriers, for example, clays; different formulations, such as of other active ingredients; polymers; and colourants) where the original shape and/or size of the seed is no longer recognizable.

Controlled release seed covering on the seeds, wherein the ingredients of the compositions are incorporated into materials that release the ingredients over time, is one of the aspects of the present invention. Examples of controlled release seed covering technologies are generally known in the art and include polymer films, waxes, or other seed coatings, wherein the ingredients may be incorporated into the controlled release material or applied between layers of materials, or both.

The methods for covering the seeds are known in the art and include dressing, dusting, slurring, foaming, soaking, coating, film-coating, or pelleting the seed with the compositions comprising repellants of the present invention. In particular, seed coating or seed pelleting are preferred according to the invention. Further, commonly known methods are described, for example in WO 2010/107312 A1 and "Applicator Training Manual for: SEED TREATMENT PEST CONTROL; Dennis M TeKrony, University of Kentucky", 1976 ERIC clearinghouse. In a preferred embodiment, the seed is covered by a method such that the germination is not negatively impacted.

Although it is believed that the methods for seed covering can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the covering would cause no biological damage to the seed.

The seed covering occurs to an unsown seed or in furrow. The term "unsown seed" is meant to include seed at any period between the harvest of the seed and the sowing of the seed in the ground for the purpose of germination and growth of the plant.

The covered seeds can be stored, handled, sowed and tilled in the same manner as any other active ingredient treated seed.

The compositions comprising repellants according to the present invention can also be used in form of a "pill" or "pellet" or a suitable substrate and placing, or sowing, the treated pill, or substrate, next to a seed. Such techniques are known in the art, particularly in EP 1 124 414, WO07/67042, and WO07/67044.

In one embodiment, the method of the present invention comprises a step of applying a herbicidally active amount of the ALS-inhibitor herbicide or an agriculturally acceptable salt or derivative thereof, to the *Brassica* crop and to the trap plants that grow from the seed according to the present invention or to their environment after the *Brassica* crop is mature enough to resist or overcome flea beetle damage.

Examples of suitable ALS inhibitors are those described herein above.

In a preferred embodiment, the ALS-inhibitor herbicide is applied after the *Brassica* crop is beyond the seedling stage, preferably at or after the two-leaf stage of the *Brassica* crop, more preferably at or after the three-leaf stage of the *Brassica* crop, most preferably at or after the four-leaf stage of the *Brassica* crop.

The ALS-inhibitor is preferably applied in form of customary types of agrochemical compositions, comprising a herbicidally active amount of said ALS-inhibitor. Examples for agrochemical composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further agrochemical compositions types are defined in the "Catalogue of pesticide formulation types and international coding system", Technical Monograph No. 2, 6th Ed. May 2008, CropLife International.

The application is preferably a spray application.

In one embodiment, the method of the present invention further comprises applying an insecticidally active amount of an insecticide I or an agriculturally acceptable salt or derivative thereof, to the *Brassica* crop and/or to the trap plants that grow from the seed according to the present invention.

Examples of suitable insecticides I include
organo(thio)phosphates: acephate, azamethiphos, azinphosmethyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chloriluazuron, cyramazin, diflubenzuron, flucycloxuron, flufenoxuron, hexaflumuron, lufenuron, novaluron, teflubenzuron, triflumuron0; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, flupyradifurone, imidacloprid, thiamethoxam, nitenpyram, acetamiprid, thiacloprid, 1-2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

ryanodine receptor inhibitors: chlorantraniliprole, cyantraniliprole, flubendiamide, N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide; N-[4-chloro-2-[(diethyl-lambda-4-sulfanylidene)-carbamoyl]-6-methyl-phenyl]-2-(3-chloro-2-pyridyl)-5-(trifluoromethyl)pyrazole-3-carboxamide; N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide; N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide; N-[4,6-dichloro-2-[(diethyl-lambda-4-sulfanylidene)carbamoyl]-phenyl]-2-(3-chloro-2-pyridyl)-5-(difluoromethyl)pyrazole-3-carboxamide; N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide; N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide; N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide;

others: benclothiaz, bifenazate, artap, flonicamid, pyridalyl, pymetrozine, sulfur, thiocyclam, cyenopyrafen, flupyrazofos, cyflumetofen, amidoflumet, imicyafos, bistrifluron, pyrifluquinazon and 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl] cyclopropaneacetic acid ester.

In another preferred embodiment, the method of the present invention further comprises applying a fungicidally active amount of a fungicide F or an agriculturally acceptable salt or derivative thereof, to the *Brassica* crop that emerged from the seed according to the present invention.

Examples of suitable fungicides F include those described herein above.

If an insecticide I and/or fungicide F are applied, the ALS-inhibitors and the active compound I and/or F can be formulated and applied jointly or separately, simultaneously or in succession.

In one embodiment, the ALS inhibitor is applied in combination with an insecticide I. In another embodiment, the ALS inhibitor is applied in combination with a fungicide F. In yet another preferred embodiment, the ALS inhibitor is applied in combination with an insecticide I and fungicide F.

A use of *Bacillus amyloliquefaciens* ssp. *plantarum* MBI600 (R.4), formerly *Bacillus subtilis* MBI600, to manage Chrysomelidae in ALS-inhibitor herbicide tolerant *Brassica* crop is one of the subjects of the present invention.

A use of *Bacillus amyloliquefaciens* ssp. *plantarum* MBI600 (R.4), formerly *Bacillus subtilis* MBI600, to manage flea beetles from the family of Chrysomelidae in *Brassica* crop is one of the subjects of the present invention.

A use of *Bacillus amyloliquefaciens* ssp. *plantarum* MBI600 (R.4), formerly *Bacillus subtilis* MBI600, to manage flea beetles from the family of Chrysomelidae in ALS-inhibitor herbicide tolerant *Brassica* crop is one of the subjects of the present invention.

Several plant-associated strains of the genus *Bacillus* have been described as belonging to the species *Bacillus amyloliquefaciens* or *Bacillus subtilis* and are used commercially to promote the growth and improve the health of crop plants (Phytopathology 96, 145-154, 2006). Recently, the strain MBI 600 that was formerly classified as *Bacillus subtilis* has been re-classified as *Bacillus amyloliquefaciens* subsp. *plantarum* based on polyphasic testing which combines classical microbiological methods relying on a mixture of traditional tools (such as culture-based methods) and molecular tools (such as genotyping and fatty acids analysis). Thus, *Bacillus amyloliquefaciens* subsp. *plantarum* MBI600 is identical to *Bacillus subtilis* MBI600 (or MBI 600 or MBI-600). For the purpose of this invention, *Bacillus subitilis* MBI 600 shall mean *Bacillus amyloliquefaciens* subsp. *plantarum* MBI600, and vice versa.

*Bacillus subtilis* MBI600 having the accession number NRRL B-50595 is deposited with the United States Department of Agriculture on Nov. 10, 2011 under the strain designation *Bacillus subtilis* 1430. It has also been deposited at The National Collections of Industrial and Marine Bacteria Ltd. (NCIB), Torry Research Station, P.O. Box 31, 135 Abbey Road, Aberdeen, AB9 8DG, Scotland under accession number 1237 on Dec. 22, 1986. *Bacillus subtilis* MBI600 is known as plant growth-promoting rice seed treatment from Int. J. Microbiol. Res. ISSN 0975-5276, 3(2) (2011), 120-130 and further described e.g. in US 2012/0149571 A1. This strain MBI600 is commercially available as liquid formulation product Integral (Becker-Underwood Inc., USA).

The bacteria *Bacillus amyloliquefaciens* and/or *Bacillus subtilis* are naturally occurring spore forming bacteria found e.g. in soils or on plant surfaces all over the world. The *Bacillus subtilis* strain MBI600 was isolated from a faba bean plant leaf surface growing at Nottingham University School of Agriculture, Sutton Bonington, United Kingdom.

*Bacillus subtilis* MBI 600 were cultivated using media and fermentation techniques known in the art, e.g. in Tryptic Soy Broth (TSB) at 27° C. for 24-72 hrs. The bacterial cells (vegetitive cells and spores) can be washed and concentrated (e.g. by centrifugation at room temperature for 15 min at 7000×g). To produce a dry formulation, bacterial cells, preferably spores were suspended in a suitable dry carrier (e.g. clay). To produce a liquid formulation, cells, preferably spores, were re-suspended in a suitable liquid carrier (e.g. water-based) to the desired spore density. The spore density number of spores per mL was determined by identifying the number of heat-resistant colony-forming units (70° C. for 10 min) on Trypticase Soy Agar after incubation for 18-24 hrs at 37 C.

*Bacillus subtilis* MBI 600 is active in temperatures between 7 C and 52° C. (Holtmann, G. 8 10 Bremer, E. (2004), J. Bacteriol. 186, 1683-1693).

The following examples are provided to illustrate the invention. These examples are not to be construed as limiting.

Field Trial:

A field trial to investigate methods for flea beetle management in *Brassica* crops was carried out under the regime of Good Experimental Practice (GEP) in Germany, federal state of Niedersachsen. The trial was set up in a 3 time replicated, one factorial randomized block design. The plot size was 45 m².

The winter oilseed rape (WOSR) variety used in the trial was the commercial hybrid "Edimax CL®" carrying a tolerance against imidazolinone herbicides. As trap plant *Sinapis alba*, variety "Ascot" was used.

All WOSR seeds had been commercially treated with the product Aatiram65®, containing the active ingredient Thiram (650 g/l), at a dose rate of 600 ml/kg seeds to protect the seed from emergence diseases.

Only the WOSR seeds for the respective plots had been treated with 160 ml/100 kg seeds with a flowable concentrate containing 8% of *Bacillus amyloliquefaciens* ssp. *plantarum* MBI600 as flea beetle repellant.

For the trap plants, no seed treatment was applied.

At the day of seeding, the trap plants were seeded first in the respective plots at a seed rate of 3.6 k/ha using a plot seeder. Afterwards, the plots with WOSR treated with Aatiram65® only were seeded, then WOSR treated on top with *Bacillus amyloliquefaciens* ssp. *plantarum* MBI600. Thus, any contamination/mixing of the different seeds and seed treatments was prevented. In both cases, a WOSR seeding rate of 50 seeds per m² was targeted.

In order to control any undesired vegetation besides the crop and the trap plants, the commercial broad spectrum herbicide Butisan Top® was applied at a dose rate of 2.0 I/ha pre-emergence of the crop and trap plants.

After the crop was mature enough to overcome flea beetle damage (2-4 true leaf stage (BBCH 12-14)), the plots were sprayed with Pulsar 40 (active ingredient Imazamox) at a dose rate of 0.875 I/ha.

The intensity of the flea beetle attack was evaluated 26 days after seeding (DAS) and 33 DAS by counting the number of crop plants with eating damage. On the first assessment, the crop plants were in 1-2 true leaf stage (BBCH 11-12), at the later assessment, the crop plants had developed to the 1-4 true leaf stage (BBCH 11-14).

Results and Interpretation

In the trial, a significant infestation with *Psylliodes chrysocephala* (PSYICH; rape flea beetle) appeared soon after the emergence of the crop.

In the plots without crop seed treatment with repellant and trap plants, the highest number of crop plants was attacked by the flea beetles at both days of assessment (Treatment 1 in Table 1).

Treatment of crop seeds with MBI600 prior to seeding did not reduce the infestation (Treatment 2 in Table 1).

A notable reduction of the number of damaged crop plants was observed in treatment 3, where *Sinapis alba* was seeded as trap plant.

Though an effect of only seed treatment with repellant was not observed, the combination of MBI600 seed treatment with the planting of trap plants resulted in the lowest number of crop plants attacked by the insects (Treatment 4 in Table 1).

TABLE 1

| | Number of crop plants with eating damage from *Psylliodes chrysocephala* (PSYICH) | | | |
|---|---|---|---|---|
| Crop treatment | plants with eating damage (26 DAS) | Stand. dev. (26 DAS) | plants with eating damage (33 DAS) | Stand. dev. (33 DAS) |
| 1. none | 33 (rel. 100) | 9 | 38 (rel. 100) | 9.7 |
| 2. MBI 600 | 34 (rel. 103) | 7.6 | 34 (rel. 91) | 7.7 |
| 3. trap plant | 23 (rel. 69) | 6.5 | 26 (rel. 69) | 9.4 |
| 4. MBI600 + trap plant | 17 (rel. 52) | 6.7 | 19 (rel. 50) | 4.6 |

In summary it was found that the combination of crop seed treatment and planting of trap plants significantly reduces the crop damage over the level of the individual measures.

Thus, farmers will be able to effectively prevent eating damage in young oilseed rape crop until the plants overcome the critical growing period.

The invention claimed is:

1. A method for managing flea beetles from the family of Chrysomelidae in a *Brassica* crop comprising the following steps
   a) planting seeds of a *Brassica* crop, which are covered by or mixed with a composition comprising a microbial pesticide from the genus *Bacillus*; and
   b) planting seeds of a trap plant, which are not covered by or mixed with a composition comprising a microbial pesticide from the genus *Bacillus*,
   wherein the microbial pesticide is *Bacillus amyloliquefaciens* ssp. *plantarum* MBI600, accession number NRRL B-50595.

2. The method according to claim 1 comprising the following steps:
   i) planting
      a) seeds of an acetolactate synthase inhibitor herbicide-tolerant *Brassica* crop, which are covered by or mixed with a composition comprising a microbial pesticide from the genus *Bacillus* and b) seeds of an acetolactate synthase inhibitor herbicide-susceptible trap plant, which are not covered by or mixed with a composition comprising a microbial pesticide from the genus *Bacillus*;

ii) applying a herbicidally active amount of an acetolactate synthase inhibitor herbicide to the *Brassica* crop and trap plants that grow from said seed or to their environment after the *Brassica* crop is mature enough to resist or overcome flea beetle damage, wherein the microbial pesticide is *Bacillus amyloliquefaciens* ssp. *plantarum* MBI600, accession number NRRL B-50595.

3. The method according to claim 2, wherein the acetolactate synthase inhibitor herbicide is selected from imidazolinone, sulfonylurea, triazolopyrimidine, pyrimidinyl oxybenzoate, and sulfonylamino carbonyl triazolinone herbicides.

4. The method according to claim 2, wherein the acetolactate synthase inhibitor herbicide is selected from imazamox or its agriculturally acceptable salts, imazapyr or its agriculturally acceptable salts, imazethapyr or its agriculturally acceptable salts, and mixtures thereof.

5. The method according to claim 2, wherein the acetolactate synthase inhibitor herbicide tolerant *Brassica* crop contains at least one AHASL trait that has a substitution(s) at least one of the positions A122(At), P197(At), R199(At), T203(At), A205(At), W574(At), S653(At), or G654(At).

6. The method according to claim 2, wherein the acetolactate synthase inhibitor herbicide-tolerant *Brassica* crop is selected from a. *Brassica napus, Brassica juncea*, or *Brassica rapa* containing an AHASL trait having the two substitutions of A122(At)T and S653(At)N;

b. *Brassica napus, Brassica juncea*, or *Brassica rapa* containing both the AHASL trait of (a) and one or two additional AHASL trait(s) that each have substitution(s) at least one of the positions A122(At), P197(At), R199(At), T203(At), A205(At), W574(At), S653(At), or G654(At);

c. *Brassica napus, Brassica juncea*, or *Brassica rapa* containing an AHASL trait having one A122(At)T substitution or one A122(At)Q substitution;

d. *Brassica napus, Brassica juncea*, or *Brassica rapa* containing both an AHASL trait having one S653(At)N substitution and an additional AHASL trait that has one substitution of A122(At)T, A122(At)Q, or W574(At)L.

7. The method according to claim 2, wherein the acetolactate synthase inhibitor herbicide is applied at or after the two-leaf stage of the *Brassica* crop.

8. Seed comprising a) seeds of a *Brassica* crop, which are covered by or mixed with a composition comprising a microbial pesticide from the genus *Bacillus*; and b) seeds of a trap plant, which are not covered by or mixed with a composition comprising a microbial pesticide from the genus *Bacillus*, wherein the microbial pesticide is *Bacillus amyloliquefaciens* ssp. *plantarum* MBI600, accession number NRRL B-50595, and wherein the seed is effective for managing flea beetles from the family of Chrysomelidae.

9. The seed according to claim 8, wherein the *Brassica* crop is acetolactate synthase inhibitor herbicide tolerant, and the trap plant is acetolactate synthase inhibitor herbicide susceptible.

10. The seed according to claim 8 in form of a mixed seed pack or as a co-pack.

11. A kit of parts comprising the seed according to claim 8 and a composition comprising an acetolactate synthase inhibitor herbicide.

12. A method for managing flea beetles from the family of Chrysomelidae in a *Brassica* crop comprising the following steps i) planting
a) seeds of an acetolactate synthase inhibitor herbicide-tolerant *Brassica* crop, which are covered by or mixed with a composition comprising a microbial pesticide from the genus *Bacillus* and
b) seeds of an acetolactate synthase inhibitor herbicide-susceptible trap plant, which are not covered by or mixed with a composition comprising a microbial pesticide from the genus *Bacillus*;

ii) applying a herbicidally active amount of an acetolactate synthase inhibitor herbicide to the *Brassica* crop and trap plants that grow from said seed or to their environment after the *Brassica* crop is mature enough to resist or overcome flea beetle damage, wherein the acetolactate synthase inhibitor herbicide tolerant *Brassica* crop contains at least one AHASL trait that has a substitution(s) at least one of the positions A122(At), P197(At), R199(At), T203(At), A205(At), W574(At), S653(At), or G654(At).

13. The method according to claim 12, wherein the acetolactate synthase inhibitor herbicide-tolerant *Brassica* crop is selected from a. *Brassica napus, Brassica juncea*, or *Brassica rapa* containing an AHASL trait having the two substitutions of A122(At)T and S653(At)N;

b. *Brassica napus, Brassica juncea*, or *Brassica rapa* containing both the AHASL trait of (a) and one or two additional AHASL trait(s) that each have substitution(s) at least one of the positions A122(At), P197(At), R199(At), T203(At), A205(At), W574(At), S653(At), or G654(At);

c. *Brassica napus, Brassica juncea*, or *Brassica rapa* containing an AHASL trait having one A122(At)T substitution or one A122(At)Q substitution;

d. *Brassica napus, Brassica juncea*, or *Brassica rapa* containing both an AHASL trait having one S653(At)N substitution and an additional AHASL trait that has one substitution of A122(At)T, A122(At)Q, or W574(At)L.

14. The method according to claim 12, wherein the microbial pesticide is selected from R.1 *Bacillus amyloliquefaciens* ssp. *plantarum* D747 (accession number FERM BP-8234), R.2 *Bacillus amyloliquefaciens* ssp. *plantarum* FZB24 (accession number DSM ID 96-2), R.3 *Bacillus amyloliquefaciens* ssp. *plantarum* FZB42 (accession number DSM 23117), R.4 *Bacillus amyloliquefaciens* ssp. *plantarum* MB1600 (accession number NRRL B-50595), R.5 *Bacillus amyloliquefaciens* ssp. *plantarum* QST-713 (accession number NRRL B-21661), R.6 *Bacillus amyloliquefaciens* ssp. *plantarum* TJ1000 (accession number ATCC BAA-390), R.7 *Bacillus firmus* I-1582 (accession number CNCM 1-1582), R.8 *Bacillus pumilus* GHA 180 (accession number IDAC 260707-01), R.9 *Bacillus pumilus* INR-7 (accession numbers NRRL B-50185 and NRRL B-50153), R.10 *Bacillus pumilus* QST 2808 (accession number NRRL B-30087), R.11 *Bacillus simplex* ABU 288 (accession number NRRL B-50340), and R.12 *Bacillus subtilis* FB17 (accession number ATCC PTA-11857).

15. Seed comprising
   a) seeds of an acetolactate synthase inhibitor herbicide-tolerant *Brassica* crop, which are covered by or mixed with a composition comprising a microbial pesticide from the genus *Bacillus*; and
   b) seeds of an acetolactate synthase inhibitor herbicide-susceptible trap plant, which are not covered by or mixed with a composition comprising a microbial pesticide from the genus *Bacillus*,
   wherein the acetolactate synthase inhibitor herbicide tolerant *Brassica* crop contains at least one AHASL trait that has a substitution(s) at least one of the positions A122(At), P1 97(At), R199(At), T203(At), A205(At), W574(At), 5653(At), or G654(At), and
   wherein the seed is effective for managing flea beetles from the family of Chrysomelidae.

16. A kit of parts comprising the seed according to claim 15 and a composition comprising an acetolactate synthase inhibitor herbicide.

17. The seed according to claim 15, wherein the microbial pesticide is selected from R.1 *Bacillus amyloliquefaciens* ssp. *plantarum* D747 (accession number FERM BP-8234), R.2 *Bacillus amyloliquefaciens* ssp. *plantarum* FZB24 (accession number DSM ID 96-2), R.3 *Bacillus amyloliquefaciens* ssp. *plantarum* FZB42 (accession number DSM 23117), R.4 *Bacillus amyloliquefaciens* ssp. *plantarum* MBI600 (accession number NRRL B-50595), R.5 *Bacillus amyloliquefaciens* ssp. *plantarum* QST-713 (accession number NRRL B-21661), R.6 *Bacillus amyloliquefaciens* ssp. *plantarum* TJ1000 (accession number ATCC BAA-390), R.7 *Bacillus firmus* I-1582 (accession number CNCM 1-1582), R.8 *Bacillus pumilus* GHA 180 (accession number IDAC 260707-01), R.9 *Bacillus pumilus* INR-7 (accession numbers NRRL B-50185 and NRRL B-50153), R.10 *Bacillus pumilus* QST 2808 (accession number NRRL B-30087), R.11 *Bacillus simplex* ABU 288 (accession number NRRL B-50340), and R.12 *Bacillus subtilis* FB17 (accession number ATCC PTA-11857).

18. The seed according to claim 15, wherein the microbial pesticide is *Bacillus amyloliquefaciens* ssp. *plantarum* MBI600, accession number NRRL B-50595 (R.4).

* * * * *

UNITED STATES PATENT AND TRADEMARK OFFICE
CERTIFICATE OF CORRECTION

PATENT NO. : 10,798,946 B2
APPLICATION NO. : 15/737512
DATED : October 13, 2020
INVENTOR(S) : Yannick Griveau et al.

It is certified that error appears in the above-identified patent and that said Letters Patent is hereby corrected as shown below:

In the Claims

At Column 26, Line 56, "MB1600" should be -- MBI600 --.

At Column 27, Line 20, "P1 97(At)," should be -- P197(At), --.

At Column 27, Line 21, "5653(At)," should be -- S653(At), --.

Signed and Sealed this
Twenty-third Day of April, 2024

Katherine Kelly Vidal
*Director of the United States Patent and Trademark Office*